(12) United States Patent
Smith

(10) Patent No.: US 9,586,381 B1
(45) Date of Patent: Mar. 7, 2017

(54) METAL PLATED OBJECT WITH BIOCIDAL PROPERTIES

(71) Applicant: Electro-Spec, Inc., Franklin, IN (US)

(72) Inventor: Jeffrey D. Smith, Bargersville, IN (US)

(73) Assignee: Steriplate, LLC, Franklin, IN (US)

( * ) Notice: Subject to any disclaimer, the term of this patent is extended or adjusted under 35 U.S.C. 154(b) by 78 days.

(21) Appl. No.: 14/522,165

(22) Filed: Oct. 23, 2014

Related U.S. Application Data

(60) Provisional application No. 61/895,644, filed on Oct. 25, 2013.

(51) Int. Cl.
| | | |
|---|---|---|
| B32B 15/20 | (2006.01) |
| B32B 15/01 | (2006.01) |
| C25D 5/16 | (2006.01) |
| C23C 28/00 | (2006.01) |
| A61L 31/08 | (2006.01) |
| A61L 31/16 | (2006.01) |
| A23L 3/3454 | (2006.01) |

(52) U.S. Cl.
CPC ............ *B32B 15/01* (2013.01); *A23L 3/3454* (2013.01); *A61L 31/088* (2013.01); *A61L 31/16* (2013.01); *C23C 28/00* (2013.01); *C25D 5/16* (2013.01); *A23V 2002/00* (2013.01); *A61L 2420/02* (2013.01)

(58) Field of Classification Search
None
See application file for complete search history.

(56) References Cited

U.S. PATENT DOCUMENTS

| | | | | |
|---|---|---|---|---|
| 2,473,886 | A | * | 6/1949 | Hull ................ B23K 35/282 420/521 |
| 4,098,610 | A | | 7/1978 | Wexell |
| 4,482,596 | A | | 11/1984 | Gulla et al. |
| 5,042,575 | A | | 8/1991 | Lindsay |
| 5,441,717 | A | | 8/1995 | Ohsumi et al. |
| 5,494,565 | A | * | 2/1996 | Schenzel ............ C23C 28/321 205/240 |
| 5,681,575 | A | | 10/1997 | Burrell et al. |

(Continued)

FOREIGN PATENT DOCUMENTS

| | | | | |
|---|---|---|---|---|
| CN | 1412329 | * | 4/2003 | ............ C22C 9/04 |
| WO | WO 2013/155618 A1 | | 10/2013 | |
| WO | WO 2013/159216 A1 | | 10/2013 | |

OTHER PUBLICATIONS

Serro et al., "A comparative study of titanium nitrides, TiN, TiNbN, TiCN, as coatings for biomedical applications", Jun. 2009, Surface & Coatings Technology, vol. 203, pp. 3701-3707.*

(Continued)

*Primary Examiner* — David Sample
*Assistant Examiner* — Seth Dumbris
(74) *Attorney, Agent, or Firm* — Bose McKinney and Evans LLP

(57) ABSTRACT

A plated object wherein the plating material has biocidal properties. The plated object can be used in a food preparation or medical care facility. The plating material includes approximately 55% copper (plus or minus 10%), 35% tin (plus or minus 10%) and 10% zinc (plus or minus 5%) by weight. In another embodiment, the plating material includes approximately 45% copper, 45% tin and 10% zinc. A method of depositing the plating material is also disclosed.

8 Claims, 14 Drawing Sheets

(56) References Cited

U.S. PATENT DOCUMENTS

| | | | |
|---|---|---|---|
| 5,770,255 A * | 6/1998 | Burrell | A01N 59/16 |
| | | | 204/192.1 |
| 5,972,526 A * | 10/1999 | Matsumoto | C23C 14/16 |
| | | | 428/643 |
| 6,080,490 A | 6/2000 | Burrell et al. | |
| 6,146,702 A | 11/2000 | Zitko | |
| 6,190,407 B1 | 2/2001 | Ogle et al. | |
| 6,273,875 B1 | 8/2001 | Siman et al. | |
| 6,365,220 B1 | 4/2002 | Burrell et al. | |
| 6,780,527 B2 * | 8/2004 | Naoi | A44C 27/006 |
| | | | 204/192.15 |
| 6,938,668 B2 | 9/2005 | Whicher et al. | |
| 7,300,673 B2 | 11/2007 | Djokic | |
| 7,427,416 B2 | 9/2008 | Gillis et al. | |
| 7,510,724 B2 | 3/2009 | Pensel | |
| 7,608,581 B2 | 10/2009 | Hamilton et al. | |
| 7,650,848 B2 | 1/2010 | Brennan et al. | |
| 7,745,509 B2 | 6/2010 | Burton et al. | |
| 7,897,266 B2 | 3/2011 | Everett, Jr. et al. | |
| 7,998,504 B2 | 8/2011 | Djokic | |
| 8,124,169 B2 | 2/2012 | Ylitalo et al. | |
| 8,309,117 B2 | 11/2012 | Rubner et al. | |
| 8,691,397 B2 | 4/2014 | Facchini et al. | |
| 8,708,978 B2 | 4/2014 | Moller et al. | |
| 8,778,408 B2 | 7/2014 | Hirota et al. | |
| 2003/0110600 A1 * | 6/2003 | Kikukawa | A44B 19/00 |
| | | | 24/399 |
| 2005/0119743 A1 | 6/2005 | Pickford et al. | |
| 2005/0202099 A1 | 9/2005 | Lo | |
| 2005/0202100 A1 | 9/2005 | Maria Dekkers et al. | |
| 2006/0246353 A1 * | 11/2006 | Guo | H01M 2/0222 |
| | | | 429/245 |
| 2006/0251730 A1 | 11/2006 | Lo | |
| 2007/0181221 A1 | 8/2007 | Pickford et al. | |
| 2008/0317800 A1 | 12/2008 | Amirzadeh-Asl | |
| 2010/0032309 A1 | 2/2010 | Pickford et al. | |
| 2010/0036501 A1 | 2/2010 | Pickford et al. | |
| 2010/0206733 A1 | 8/2010 | Agg et al. | |
| 2011/0256356 A1 * | 10/2011 | Tomantschger | C25D 1/00 |
| | | | 428/172 |
| 2012/0171406 A1 * | 7/2012 | Mase | A61L 15/18 |
| | | | 428/76 |
| 2012/0321686 A1 | 12/2012 | Bokorny et al. | |
| 2013/0004585 A1 | 1/2013 | Crudden et al. | |
| 2013/0014671 A1 | 1/2013 | Tzeng | |
| 2013/0216169 A1 * | 8/2013 | Zidar | C22C 9/00 |
| | | | 384/276 |
| 2014/0141263 A1 | 5/2014 | Jones et al. | |
| 2014/0147332 A1 | 5/2014 | Murray et al. | |

OTHER PUBLICATIONS

Written Testimony of Jeffrey D. Smith President/CEO of Electro-Spec, Inc. and President of Steriplate, LLC submitted to the Subcommittee on Research and Technology Committee on Science, Space and Technology for the hearing entitled Technology for Patient Safety at Veterans Hospitals, U.S. House of Representatives, Washington, D.C., Jun. 26, 2014 (15 pages).

Evaluating the Feasibility of Reducing Surface Contamination in Healthcare Facilities with Micro-Pattern Films, May et al., CHICAACGO Presentation, 51st ICAAC, Sep. 17-20, 2011, Chicago, IL.

Emergence of superhydrophobic behavior on vertically aligned nanocone arrays, D'Urso et al., Applied Physics Letters, 90, 044102 (2007).

Guide to Tri-MTM Plating, Electro-Spec, Inc., Franklin, Indiana, at least as early as Oct. 24, 2012 (4 pages).

Tri-M3TM (Tri-Alloy, Tri-Metal or White Bronze) Plating, Electro-Spec, Inc., Franklin, Indiana, at least as early as Oct. 24, 2012 (3 pages).

Telecommunications Plating, Electro-Spec, Inc., Franklin, Indiana, at least as early as Oct. 24, 2012 (2 pages).

SAM's Technology (Self Assembled Molecules), Electro-Spec, Inc., Franklin, Indiana, at least as early as Oct. 24, 2012 (1 page).

* cited by examiner

| Significant Parameters | Summary: Effect of Parameters on Alloy Composition | |
|---|---|---|
| | Increase | Decrease |
| KOH | Cu ↑<br>Sn ↓<br>Zn ↑ | Cu ↓<br>Sn ↑<br>Zn ↓ |
| Temp °F | Cu ↓<br>Sn ↑<br>Zn ↓ | Cu ↑<br>Sn ↓<br>Zn ↑ |
| KCN | Cu ↓<br>Sn ↑<br>Zn ↓ | Cu ↑<br>Sn ↓<br>Zn ↑ |
| Current Density | Cu ↑<br>Sn ↓<br>Zn ↓ | Cu ↓<br>Sn ↑<br>Zn ↑ |

*Fig. 6*

Summary: Effect of Parameters on Color of the Deposit

| Color | Grey | White | Yellow |
|---|---|---|---|
| Cu | ↘ | — | ↗ |
| Sn | ↗ | — | ↘ |
| KOH | ↘ | — | ↗ |
| KCN | ↗ | — | ↘ |
| Temp °F | ↗ | — | ↘ |
| Current Density | ↘ | — | ↗ |

*Fig. 7*

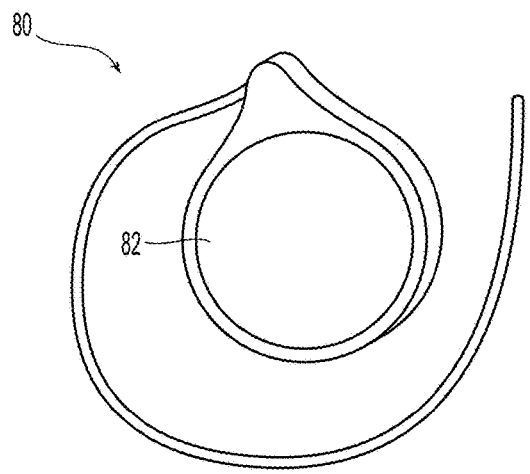
*Fig. 21*
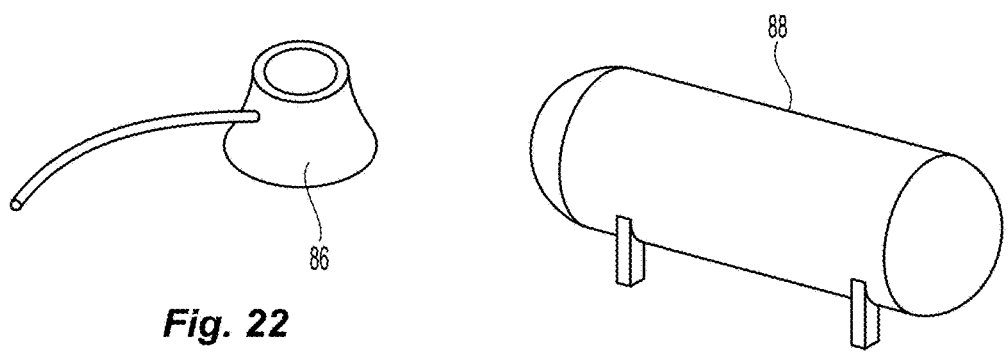
*Fig. 22*
*Fig. 23*
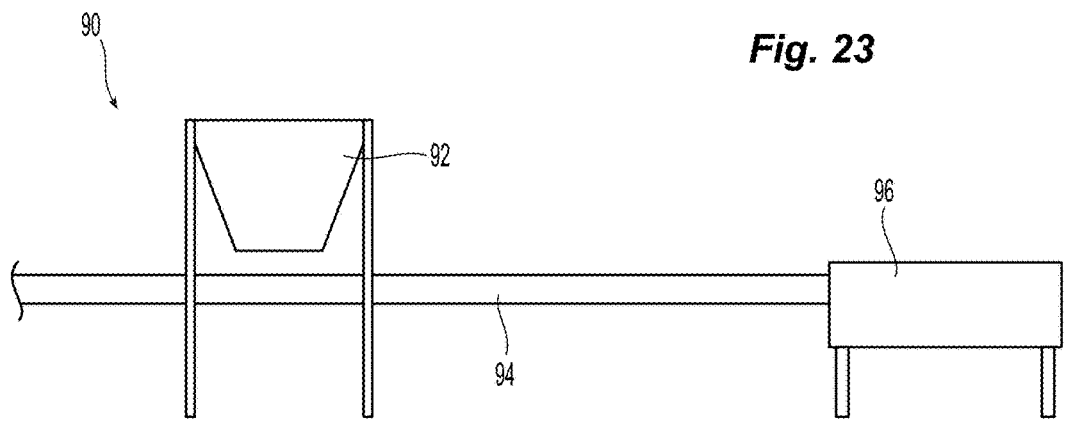
*Fig. 24*

METAL PLATED OBJECT WITH BIOCIDAL PROPERTIES

CROSS REFERENCE TO RELATED APPLICATIONS

This application claims priority under 35 U.S.C. 119(e) of U.S. provisional patent application Ser. No. 61/895,644 filed on Oct. 25, 2013 entitled METAL PLATING WITH BIOCIDAL PROPERTIES the disclosure of which is hereby incorporated herein by reference.

BACKGROUND

The present invention relates to metal plating and, more specifically, to metal plating objects to provide them with biocidal qualities.

Nosocomial infections or "hospital-acquired infections" are one of the most lethal killers of hospital patients. In the United States alone, it is estimated that 1 in 9 patients (2 million patients per year) are infected by some form of potentially lethal germs or bacteria during their treatment and stay. Unfortunately, it is believed that 90,000 to 100,000 people a year die due to these infections or complications from infections.

Oftentimes bacteria and other harmful microbes are resident on surfaces that are handled, introduced into a body or otherwise contacted in a manner that allows for the transfer of the microbes and resulting infection of a person or animal. While hospitals and other healthcare facilities present a concern with regard to such surfaces, other facilities, such as food handling facilities, may also present similar concerns.

Reducing the number of infections which result from the transfer of microbes from such surfaces is clearly desirable.

SUMMARY OF THE INVENTION

The present invention provides a metal plating with biocidal properties that can be used to inhibit infections.

Pathogenic enteric germs and bacteria must have a certain type of environment to exist long enough to be transferred from one location to another. These bacteria, such as salmonellae, hepatitis, staphylococci, *e. coli*, etc., can be transferred in many different ways and can survive on many different types of surfaces for extended periods of time. The most significant mode of transfer is via contaminated hands, which come in contact with hardware parts such as door handles, faucets, sinks, medical equipment, fittings, furniture and many other types of hardware. If the conditions are suitable for the survival and growth of bacteria, the bacteria can be easily transmitted by contact with such hardware. In an environment where there are a large number of sick people whose immune systems are weakened, this provides an opportunity for the transmission of these potentially lethal bacteria and germs. Medical staff moving from patient to patient, medical procedures that bypass the body's natural protective barriers, and poor sanitation regarding uniforms, equipment sterilization and other preventive measures can compound the situation.

Preventing all human contact with such hardware in a treatment facility or hospital is, of course, not possible. However, inhibiting or preventing the growth of these bacteria and ultimately their transmission can be facilitated with the use of the plating material disclosed herein.

The plating material has anti-microbial properties and has the potential to limit the growth and/or kill bacteria and germs that come into contact with it. The plating material is an alloy which includes copper, tin and zinc. Both copper and tin have germicidal properties. Copper has even been shown to be effective against methicillin-resistant *staphylococcus aureus* ("MRSA") which is one of the more lethal strains of antibiotic resistant bacteria in existence today.

While copper will oxidize and tarnish over time, the copper containing alloy of the present application is resistant to oxidation. As a result, the disclosed alloy can generally withstand the use of cleaners, disinfectants and other solutions used to "sterilize" surfaces. The alloy can also be used to provide a uniform and bright surface and may have an appearance similar to nickel or stainless steel.

In one embodiment, the plating material includes approximately 55% copper (plus or minus 10%), 35% tin (plus or minus 10%) and 10% zinc (plus or minus 5%) by weight. In another embodiment, the plating material includes approximately 45% copper, 45% tin and 10% zinc (by weight). A surface treatment which includes a surfactant (1-5% by weight) and/or ethanol (0.1-10% by weight) may also be used with the plating layer.

The invention comprises, in one form thereof, a device for inhibiting the transmission of microorganisms which includes a metal object adapted for use in an environment where the transmission of microorganisms is undesirable and a metal plating disposed on the metal object and forming at least a portion of the exterior surface of the object. The metal plating includes (by weight): copper within a range of about 45% to about 65%; tin within a range of about 25% to about 45%; and zinc within a range of about 5% to about 15%.

In some embodiments, the device is adapted to be implanted in a living organism. For example, the device may be an orthopedic implant such as an orthopedic rod. The device might alternatively take the form of at least a portion of a stent, a catheter, a shunt or a baclofen pump.

In other embodiments, the device might be orthopedic hardware adapted for use either in an implanted condition or external to the patient.

In other embodiments, the device may be a part of a plumbing system, a piece of medical equipment, or food processing system. In some embodiments the device is a door handle.

In some applications, a hydrophobic surface treatment layer may advantageously be provided on the metal plating. In other applications, it may be advantageous to provide a hydrophilic treatment layer on the metal plating.

The invention comprises, in another form thereof, a method of inhibiting the transmission of microorganisms in a food processing or medical care facility. The method includes providing a metal object for use within the facility; forming a metal plating on the metal object wherein the metal plating comprises (by weight): copper within a range of about 45% to about 65%; tin within a range of about 25% to about 45%; and zinc within a range of about 5% to about 15%.

In some embodiments, the metal plating includes no more than approximately 55% copper. In still other embodiments, the metal plating comprises copper within a range of about 45% to about 50%; tin within a range of about 40% to about 45%; and zinc within a range of about 5% to about 10%. For example the metal plating may include approximately 45% copper, approximately 45% tin and approximately 10% zinc. (Unless explicitly stated otherwise, all percentages of the metals comprising the plating layer used herein are by weight.)

In some embodiments, the finished surface of the metal plating is mechanically unprocessed. In those embodiments having a hydrophobic or hydrophilic surface treatment layer formed on the metal plating, it can be advantageous in some applications to have the exterior surface of the metal plating be mechanically unprocessed when the surface treatment layer is formed thereon. Mechanically unprocessed surfaces will define small scale irregularities which are thought to enhance the biocidal properties of the surface.

BRIEF DESCRIPTION OF THE DRAWINGS

The above mentioned and other features of this invention, and the manner of attaining them, will become more apparent and the invention itself will be better understood by reference to the following description of embodiments of the invention taken in conjunction with the accompanying drawings, wherein:

FIG. 6 is a chart depicting how various parameters impact the composition of the plating layer.

FIG. 7 is a chart depicting how various parameters impact the color of the plating layer.

FIG. 21 is a schematic depiction of a baclofen pump.

FIG. 22 is a schematic depiction of an implantable dialysis port.

FIG. 23 is a schematic depiction of a food handling storage vessel.

FIG. 24 is a schematic depiction of a food handling process line.

Figure 1:
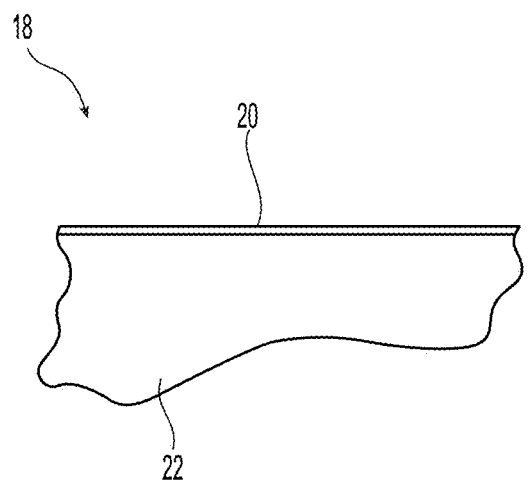
FIG. 1 is a schematic view of an object having a biocidal plating layer.

Corresponding reference characters indicate corresponding parts throughout the several views. Although the exemplification set out herein illustrates an embodiment of the invention, in one form, the embodiment disclosed below is not intended to be exhaustive or to be construed as limiting the scope of the invention to the precise form disclosed.

DETAILED DESCRIPTION OF THE INVENTION

A plated object 18 having a plating layer 20 deposited on a metal substrate 22 wherein plating layer 20 has biocidal properties is schematically depicted in FIG. 1. The plating layer may have a composition (by weight) that is approximately 55% copper (plus or minus 10%), 35% tin (plus or minus 10%) and 10% zinc (plus or minus 5%). In other embodiments, the plating layer may have a composition (by weight) wherein the amount of copper is within a range of about 45% to about 50%; tin is within a range of about 40% to about 45%; and zinc is within a range of about 5% to about 10%. In an exemplary embodiment, the plating layer is 45% copper, 45% tin and 10% zinc. A surface treatment which includes a surfactant (1-5% by weight) and/or ethanol (0.1-10% by weight) may also be used with the plating layer. In addition to its biocidal properties, the disclosed plating layer has several other advantageous properties.

Figure 2:
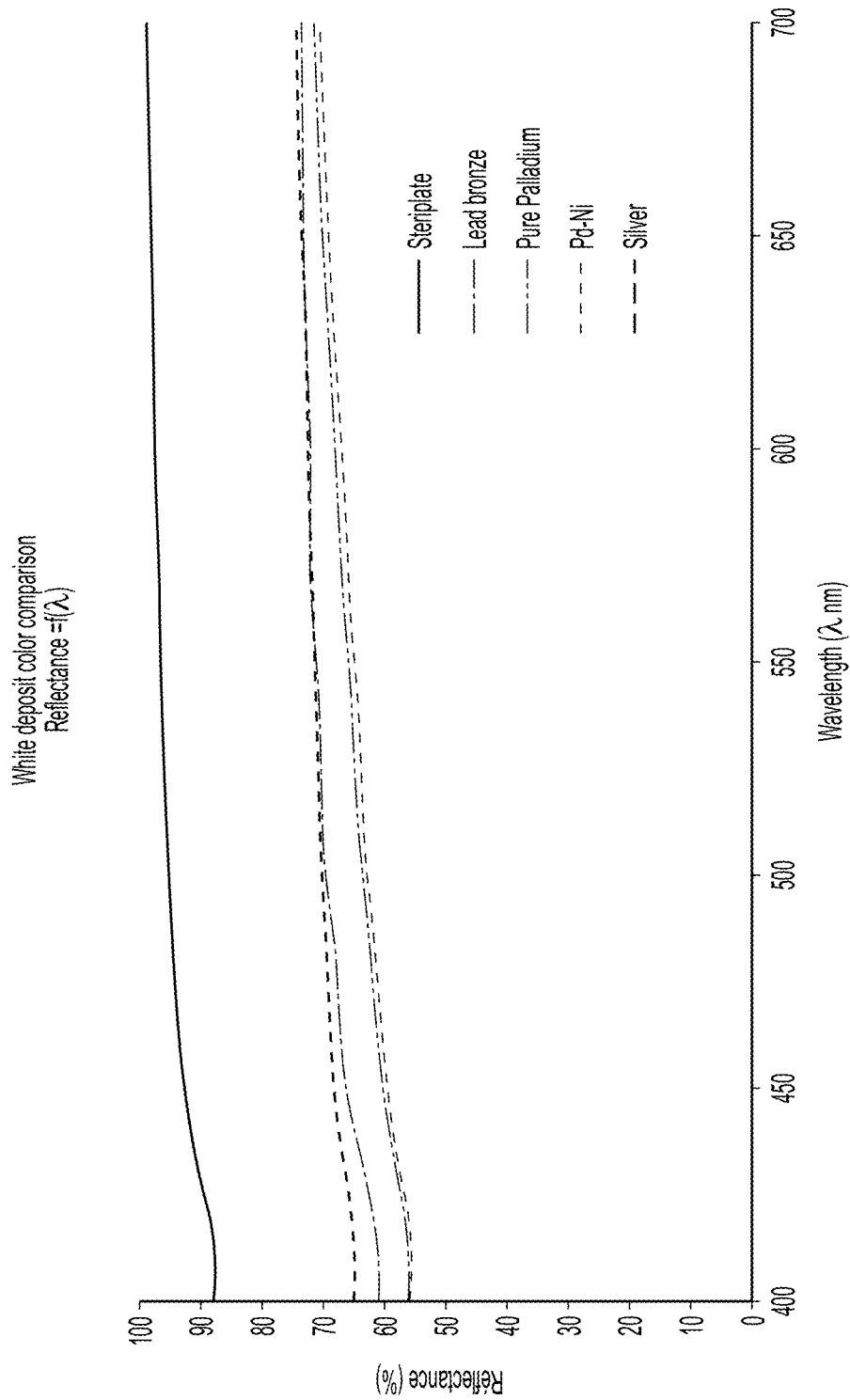
FIG. 2 is a chart representing the light reflectance of the plating layer and that of several other surfaces.

The plating layer has an aesthetically pleasing surface similar in appearance to nickel or stainless steel and provides a uniform and bright surface. When subject to a white deposit color comparison using a Minolta Colorimeter, the plated surface displayed a reflectance of approximate 65% at a wavelength ($\lambda$) of 400 nm. As the wavelength was increased, the reflectance also increased reaching a reflectance of slightly greater than 70% at a wavelength ($\lambda$) of 700 nm. FIG. 2 is a chart representing the results of the reflectance test.

The plating layer, unlike copper, is resistant to oxidation and therefore does not easily tarnish and has good resistance to corrosion caused by hand perspiration. These properties make the plating layer well suited for use on handles and other objects that are frequently handled by users. The corrosion resistance of the plating layer allows it to be subjected to cleaners, disinfectants and similar sterilization solutions that are typically used in food preparation and medical care facilities where the transfer of microorganisms presents dangers.

Figure 3:
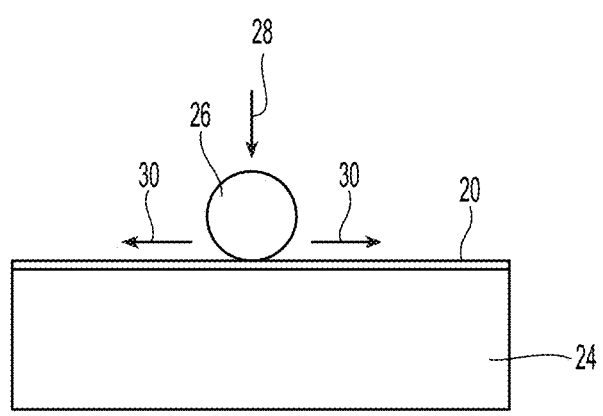
FIG. 3 is a schematic depiction of wear resistance testing procedure.
Figure 4A:
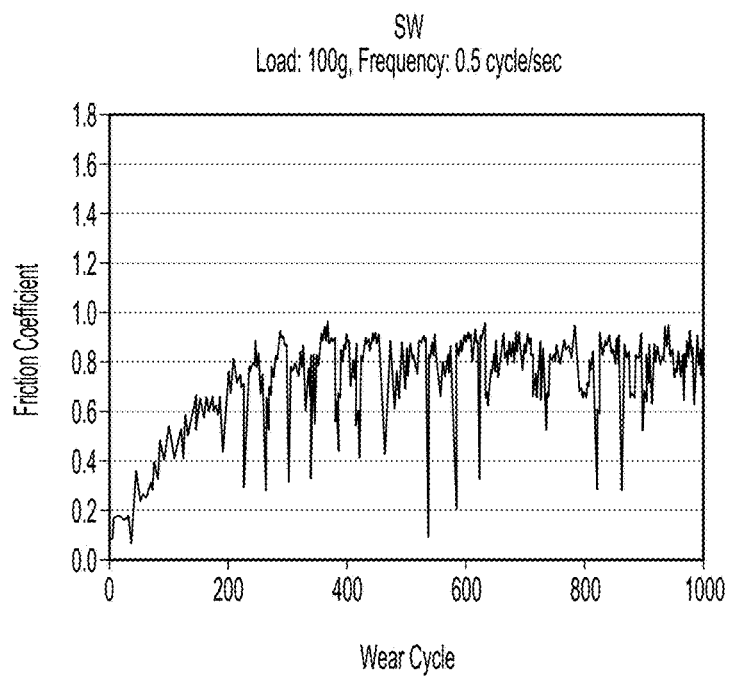
FIG. 4A is a chart depicting the results of a wear resistance test.

FIGS. 3 and 4A concern the wear resistance of the plating layer. FIG. 3 schematically depicts how a sliding wear test is performed on plated object 18. A layer of plating material 20 is formed on metal substrate 24 which takes the form of a copper disk. A spherical rider 26 having a diameter of 4 mm takes the form of copper sphere with a plating layer formed thereon that is the same as plating layer 20 formed on disk 24. A 100 g load is applied to rider 26 in a direction perpendicular to plating layer 20 formed on disk 24 as represented by arrow 28. Rider 26 is subjected to reciprocal motion at a frequency of 0.5 Hz and an amplitude of 14 mm for 1000 cycles as represented by arrows 30. The frictional coefficient is measured and FIG. 4 is a chart representing the results of the test. As can be seen in FIG. 4A, the frictional coefficient rises from an initial value of approximately 0.2 to a value of approximately 0.8 after roughly 200 cycles. The value of the frictional coefficient varies about 0.8 during the interval between 200 and 1000 cycles.

Figure 4B:
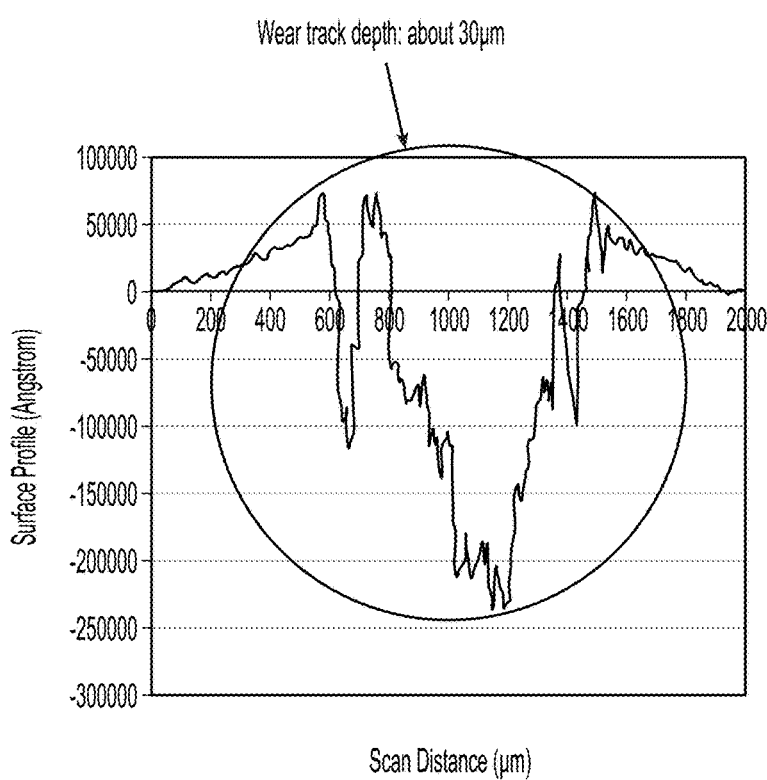
FIG. 4B is a chart depicting the surface profile of a copper surface having a wear track.
Figure 4C:
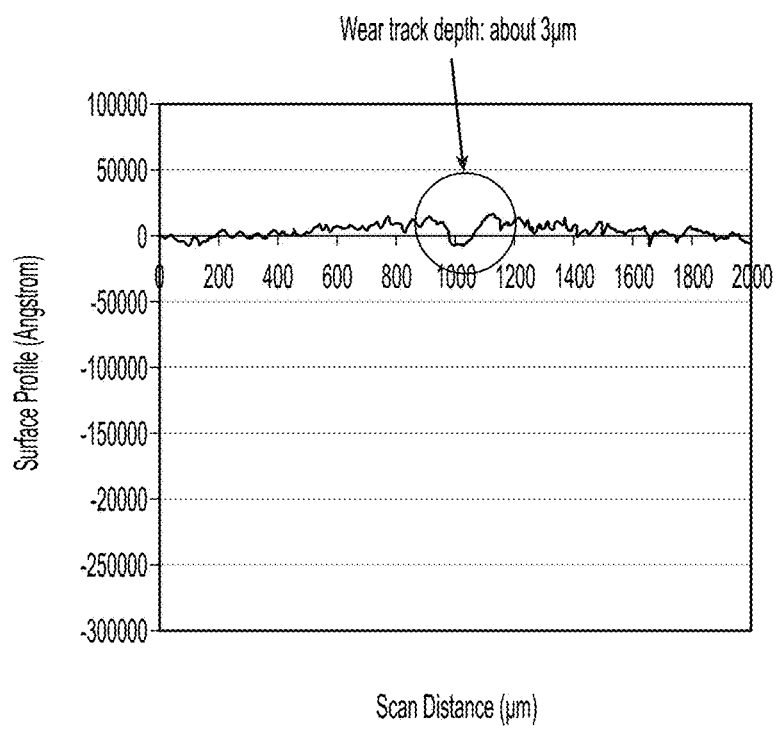
FIG. 4C is a chart depicting the surface profile of a plated surface having a wear track.
Figure 4D:
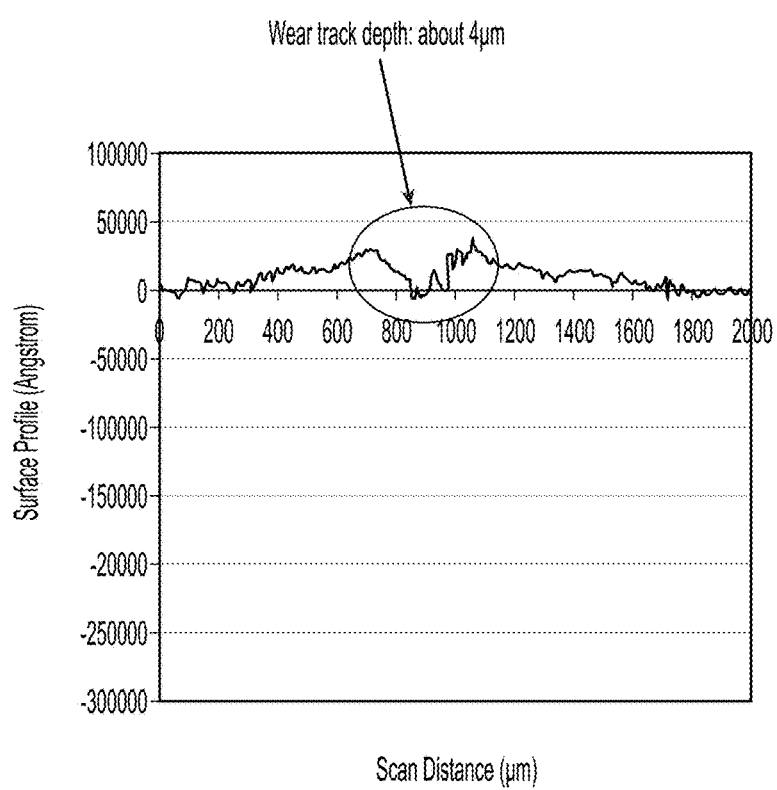
FIG. 4D is a chart depicting another surface profile of a plated surface having a wear track.

FIGS. 4B-4D present charts showing three examples of surface profiles resulting from subjecting surfaces to a wear test as described above with reference to FIG. 3. FIG. 4B presents the surface profile of a copper surface which developed a wear track having a depth of approximately 30 micrometers. FIG. 4C presents the surface of a first example of plating layer 20 which developed a wear track with a depth of approximately 3 micrometers and FIG. 4D presents the surface of a second example of plating layer 20 which developed a wear track with a depth of approximately 4 micrometers. As can be seen from FIGS. 4B-4D, plating 20 provides a wear resistant surface.

The exemplary embodiment of plating layer 20 has a hardness (Vickers) of approximately 450-500 $Hv_{0.05}$. It has a specific gravity ($g/cm^3$) of approximately 8.2-8.5. The plating layer is electrically conductive and non-magnetic.

Plating layer 20 also displayed excellent corrosion resistance as will be recognized by those having ordinary skill in the art upon review of the following test results for plating layer 20:

artificial sweat (ISO 3160): <24 h
thioacetamide: >24 h
NSS: brass: 48 H to white rust, >122 H
humid atmosphere (85° C.-85% RH): >72 Hrs
thermal cycles: −50° C./+85° C., RH=70% for 10 days (1000 cycles): no discoloration
tarnish resistance: no color change after 4 H exposure at 150° C.

Copper and tin are both known to have biocidal properties and the alloy forming plating layer 20 includes both copper and tin. As a result, plating layer 20 also possesses biocidal properties and can inhibit the growth and potentially kill many forms of bacteria, fungus, germs and other microorganisms. For example, a plating layer 20 having a thickness of approximately 0.000050 inches (0.00013 cm) applied to a brass panel provided positive results within an hour when exposed to *staphylococcus aureus* germs. Additional testing has shown that a plating 20 was able to achieve antimicrobial functionality against *S. aureus* (MRSA) at an 99.99% reduction in just 6 hours of exposure. In another test, a plating layer 20 demonstrated anti-microbial functionality against *E. coli* achieving a 99.9969% reduction. Further testing showed that a plating layer 20 was able to achieve antimicrobial functionality against *E. coli* (CRE) at greater than 99.9998% reduction in 24 hours. Other testing involving plating layer 20 has also demonstrated a 90% reduction in spore colonies including effectiveness against a disinfectant resistant endospore. Assuming a patient exposure of 2.5 grams of plating layer 20, this would be below levels of toxicological concern. With regard to MEM cytotoxicity, plating layer 20 is not cytotoxic.

A method of forming a plating layer 20 by electroplating will now be discussed. One embodiment of the bath makeup that may be used is CuCN 72 g/liter; Sn 18 g/liter; ZnCN 22 g/liter; KCN 300 g/liter; KOH 20 g/liter and an organic brightener and organic wetter wherein the organic brightener and organic wetter are provided in a ratio of 0.4 liter organic brightener to 1.0 liter of organic wetter. The operating parameters of the bath are advantageously maintained within the following ranges: CuCN 12.5-18 g/liter; Sn 14-28 g/liter; ZnCN 3.0-6.0 g/liter; CN 50-70 g/liter; and KOH 15-25 g/liter.

The bath is not very sensitive to metallic contamination. Rinsing the pieces well before plating, however, facilitates good quality work and helps prevent contamination of the bath. Ni (<15 ppm) and Cr are potentially harmful contaminants and can be introduced by the use of stainless steel anodes. As a result, the use of insoluble anodes will generally provide more desirable results.

Figure 5:
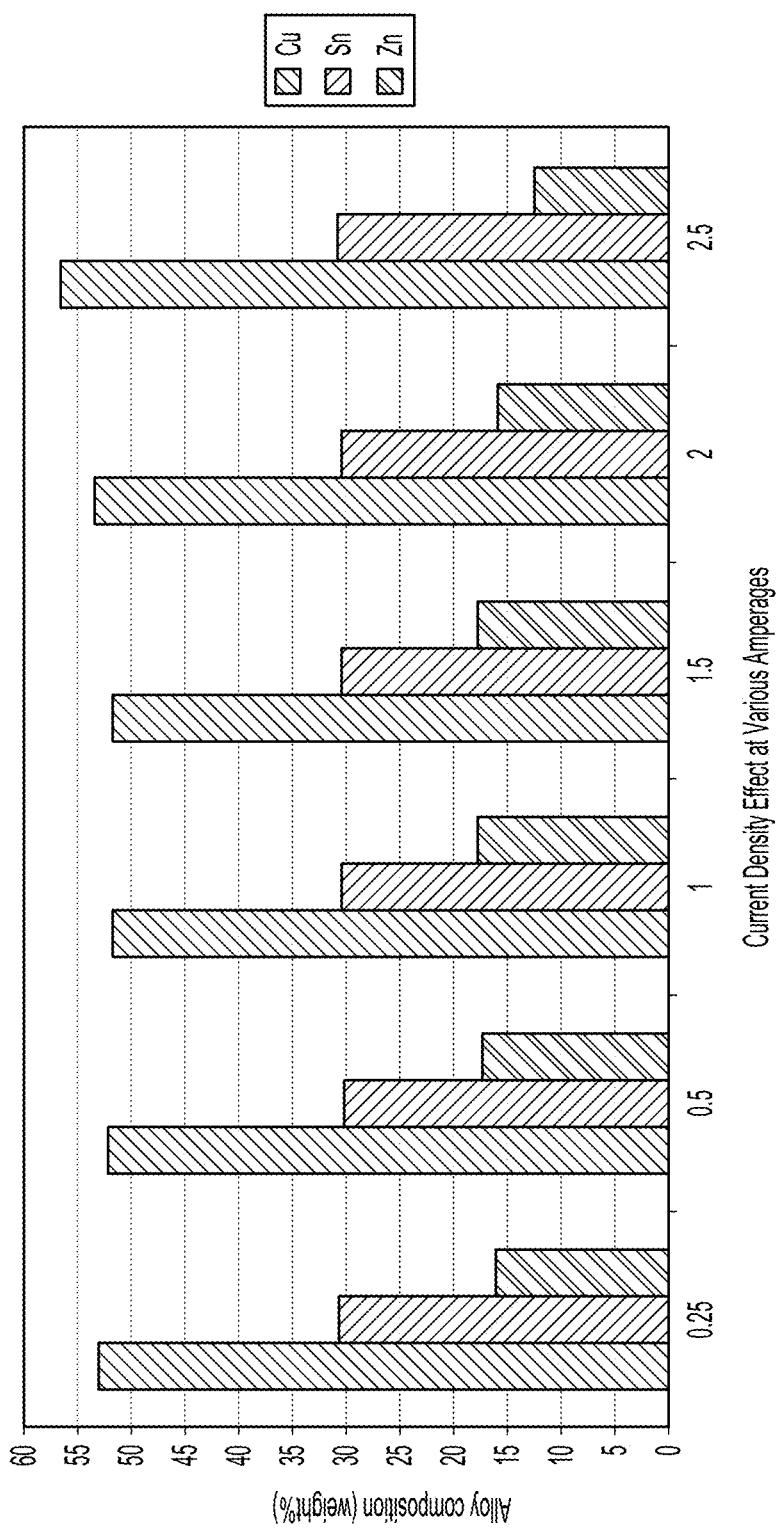
FIG. 5 is a chart depicting how current density can impact the composition of the plating layer.

Current density has an impact on the composition of the plating layer. When the current density is too low this can result in a yellowish deposit. This effect can potentially be overcome by the addition of 2 g/liter of KCN. When the current density is excessive, the plating layer can become yellow and hazy. A chart depicting how current density can impact the composition of the plating layer is shown in FIG. 5.

A chart depicting how several significant parameters can impact the composition of the plating layer is provided in FIG. 6. As can be seen from this chart, increasing the concentration of KOH in the bath increases the percentage of copper and zinc in the plating layer while decreasing the percentage of tin. The decrease of KOH has the opposite effect. Increasing the temperature increases the amount of tin in the plating layer while decreasing that of copper and zinc. Decreasing the temperature has the opposite effect. Increasing the concentration of KCN in the bath decreases the percentage of copper and increases the percentage of tin while not impacting the percentage of zinc in the plating layer. Decreasing the concentration of KCN increases the percentage of copper, decreases that of tin and has no impact on the amount of zinc. Increasing the current density increases the percentage of copper in the plating layer, decreases the percentage of tin and does not alter the percentage of zinc. Decreasing the current density decreases the percentage of copper, increases the percentage of tin and does not impact that of zinc.

A chart depicting how various parameters impact the color of the plating layer is provided in FIG. 7. As can be seen in this chart, increasing the percentage of copper in the plating layer decreases the grey color and increases the yellow color of the plating layer. Increasing the percentage of tin in the alloy forming the plating layer increases the grey and decreases the yellow color of the plating layer. Consequently, increasing the concentration of KOH in the bath will decrease the grey and increase the yellow color of the resulting plating layer. Increasing the concentration of KCN will increase the grey and decrease the yellow of the plating layer. Increasing the temperature of the bath will increase the grey and decrease the yellow color of the resulting plating layer while increasing the current density will decrease the grey and increase the yellow color of the plating layer deposited on the piece.

Figure 8A:
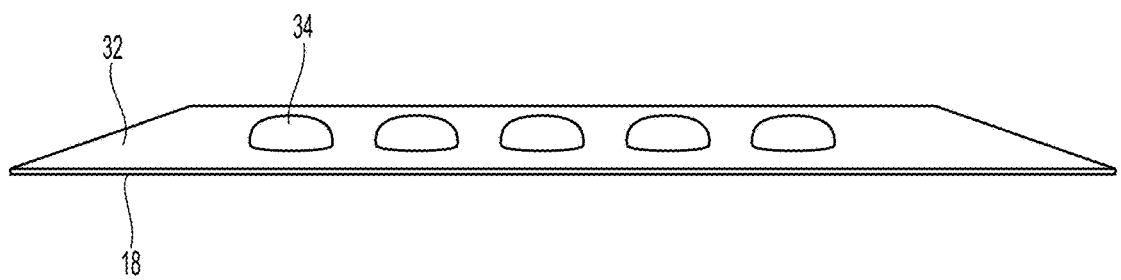
FIG. 8A is a schematic depiction of beaded water on a hydrophobic surface.
Figure 8B:
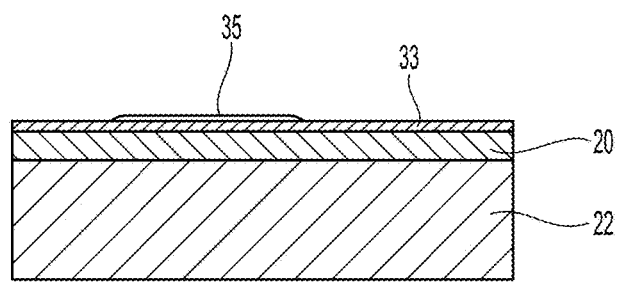
FIG. 8B is a schematic depiction of water on a hydrophilic surface.
Figure 9:
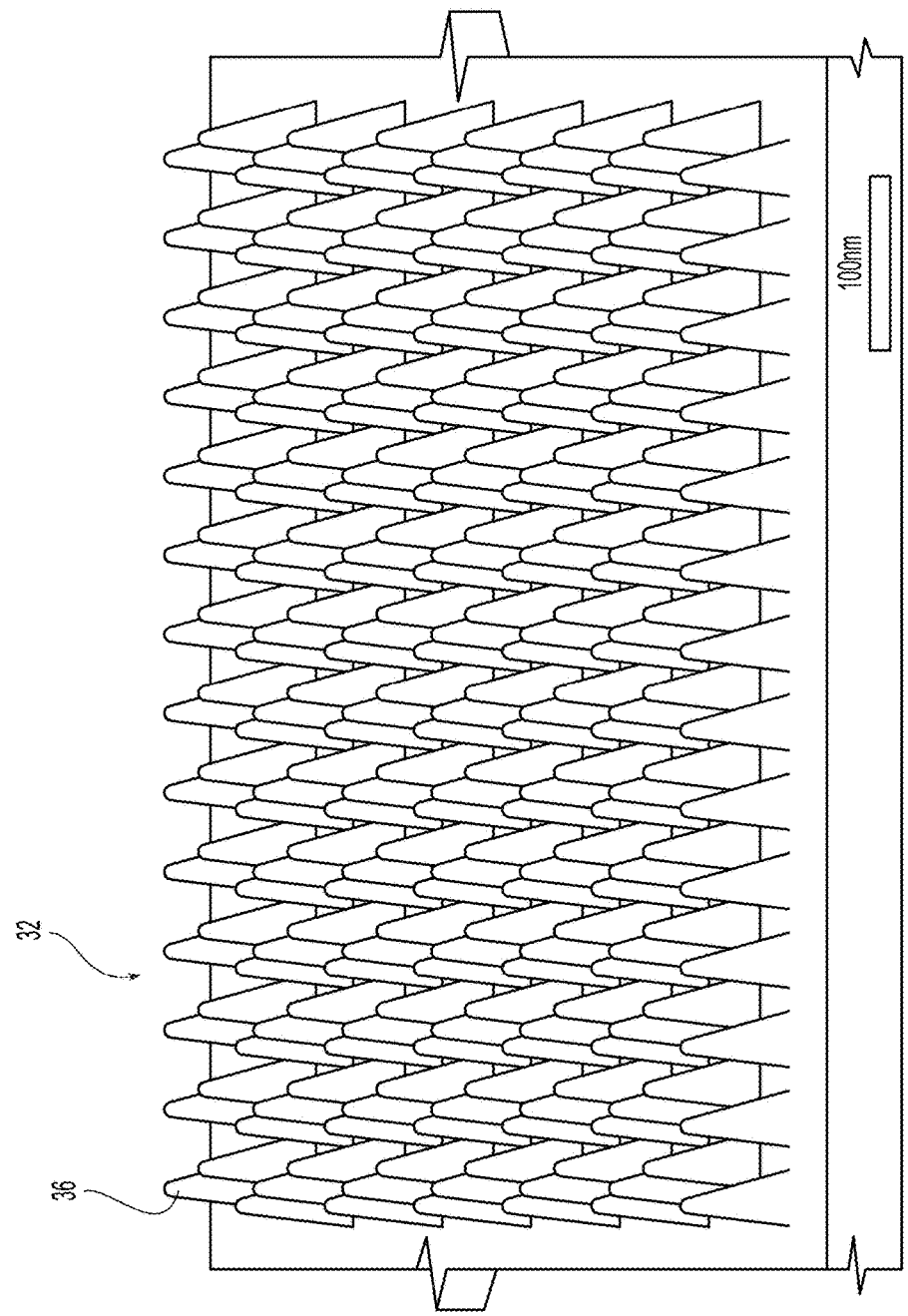
FIG. 9 is a schematic depiction of a surface having nano-cones to provide a hydrophobic surface.

It may also be beneficial in some circumstances to provide plated object 18 with a hydrophobic surface treatment layer 32. FIG. 8 schematically depicts water beads 34 on a plated object having a surface which has been treated to provide it with hydrophobic properties. There are various different methods that can be used to provide plating 20 with hydrophobic properties. One particularly effective manner of providing a hydrophobic surface is the use of self-assembling molecules (SAMs). FIG. 9 schematically depicts how SAMs can be used to form nano-cones 36 having hydrophobic properties.

The hydrophobic surface treatment layer may be formed using any suitable materials and methods. A variety of materials are commercially available for forming hydrophobic surfaces. One example of such a surface treatment that may be used with metal plating 20 is formed using Bronzex® Nano 1000W a product commercially available from Enthone, a subsidiary of Cookson Group PLC and having a place of business in Surrey, England. This material includes 1-5% (by weight) of a surfactant/alkane thiol mixture and 0.1-1.0% (by weight) of a proprietary alcohol. The application of the hydrophobic layer includes immersing the plated layer 20 in a bath of the material at 120° F. to 125° F. for 10 minutes with vigorous mechanical agitation. This is followed by two deionized water rinses for 2 to 3 minutes at ambient temperature. Then a hot (150° F. to 160°) deionized water rinse for 1 to 2 minutes and then a centrifugal dry for 10 minutes.

Plating layer 20 may alternatively have a hydrophilic surface treatment layer 33 which has been treated to provide it with hydrophilic properties. For example, the plating layer 20 may be immersed in suitable hydrophilic material bath, rinsed and dried. The intended use of the plated object will determine whether it is more advantageous for the surface to be hydrophobic or hydrophilic. It is noted that the schematic depictions of surface treatment layers 32, 33 indicate that such layers completely cover plating layer 20. This is a graphical oversimplification, when provided with a hydrophobic or hydrophilic surface treatment layer 32, 33, the surface treatment layer is a thin layer that does not foreclose all interaction between the underlying plating layer 20 and microbes in the external environment.

In this regard, it is noted that there may be some surface area of plating layer 20 that is not covered by the surface treatment layer, e.g., area between the cones schematically depicted in FIG. 9. It is also noted that it is thought that metal plating 20 destroys bacteria and other microbes by coaxing the organism to donate electrons to metal plating thereby resulting in the production of free radicals within the cell whereafter the free radicals inflict damage to bacterial DNA and cell proteins. This mechanism merely requires that the microbes and metal plating be relatively positioned whereby the metal plating 20 can attract electrons from the microbes. It is believed that this mechanism can be effective with a thin hydrophobic or hydrophilic surface treatment layer disposed on the external surface of metal plating 20.

Figure 25:
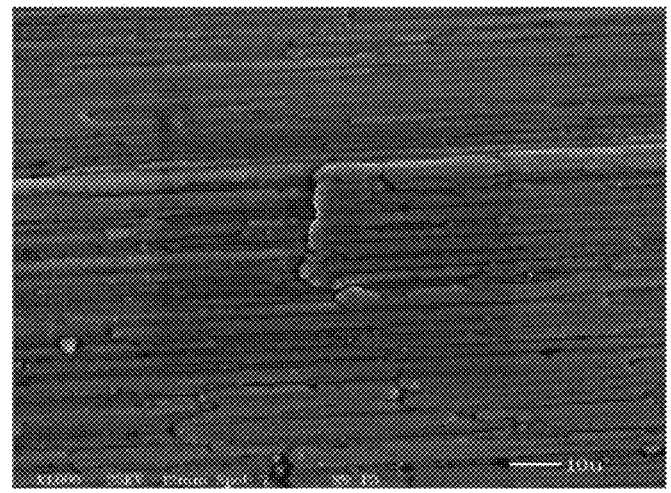
FIG. 25 is a scanning electron microscope image showing the surface topography of a plating layer.
Figure 26:
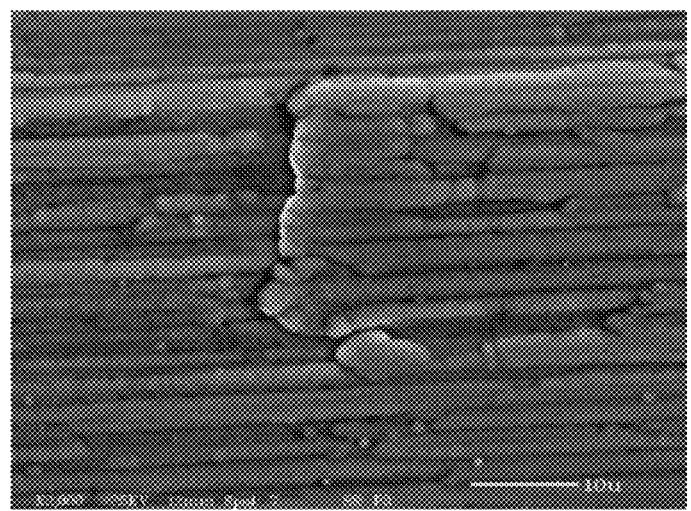
FIG. 26 is another scanning electron microscope image showing the surface topography of a plating layer.

It is further noted that the plating process described herein will often leave plated surface 20 with a surface topography formed by small ridges and valleys or other small scale irregularities. This is a function of the current density and the resulting copper density and grain structure. Stamped and machined copper surfaces typically have a smoother and more regular surface topography. In many circumstances it is thought that providing a plating layer 20 with an external surface that has been subject to only minimal or no further mechanical processing to thereby leave the surface with a topography having small scale irregularities will be advantageous. FIGS. 25 and 26 are images obtained with a scanning electron microscope of a plating layer 20 showing small scale irregularities. FIG. 25 is an image that was originally at 1000:1 scale while FIG. 26 was originally 2000:1 scale. It is thought that such small scale irregularities may enhance the anti-microbial effects of the surface when the irregularities are on a scale that is smaller than the organism of concern. The presence of such small scale irregularities in the surface can deny bacterium and other microbes a "flat" surface to land and instead require the organism to attach to limited and separated areas of attachment (e.g, the top of adjacent ridges). This is thought to cause mechanical stress on the organism and thereby discourage the organism from settling on and colonizing the surface.

One of the more important aspects of making a surface resistant to microbial "loading" is to ensure that the surface is dry. By making plating layer 20 hydrophilic (readily attracting water), the surface will have a propensity to dry quicker, rather than "pooling" the liquid on certain areas of the surface. When surfaces experience this "pooling" or beading of the liquid, the surface is likely to dry unevenly with the pools of liquid drying more slowly and thereby result in the continued loading of microbes in the surfaces areas subject to the pooling of the liquid. For plated objects intended for use outside the body of a living organism, treating the external surface of plating 20 to render it hydrophilic can promote the rapid drying of the surface and thereby enhance its antimicrobial efficacy.

In contrast, for plated objects that are intended to be at least partially implanted in a living organism, e.g., a human being, for either a short or long duration of time, it may be desirable to provide such objects with a hydrophobic surface treatment. The hydrophobic properties of such a surface can affect the interaction between the surface and such bodily fluids as blood, mucous, saliva, urine, perspiration as well as other associated and potentially contaminated fluids and limit the adherence of such liquids to the surface and formation of biofilms thereon. It is also thought, although not yet demonstrated, that providing a plating 20 with hydrophobic properties on an implantable object could potentially act as an anticoagulant and help prevent clotting and strokes. It is also thought it may be useful in treating or preventing thrombosis. In this regard, it is noted that such a treatment on a stent 38 could provide particularly significant benefits.

The use of a plating layer 20 in a food preparation/handling facility or a medical care facility has the potential to inhibit the growth and transmission of potentially harmful microorganisms. For example, a plating layer 20 could be applied to the handles used on the doors, plumbing fixtures and furniture in a medical care facility. For example, plating layer 20 could be applied to not only the plumbing fixture handles but also the plumbing structure which is exposed but not generally touched by users. A plating layer 20 could also be applied to the knobs, switches and housings of medical equipment used in a medical care facility. It could also be applied to the knobs, switches and housing of non-medical equipment that is intended for use in a medical care facility. Beds and other support structures found in medical care facilities often include metallic members which could also benefit from being plated with plating layer 20. Other metallic surfaces found in medical care facilities could also benefit by being provided with a biocidal plating layer 20. Additionally, many medical instruments and implanted objects that directly contact the medical care provider and/or the patient could also benefit by being provided with a plating layer 20.

Similarly, in a food preparation facility the exposed metallic surfaces and tools used in the facility could be plated with a plating layer 20 to inhibit the growth and transmission of potentially harmful microorganisms.

FIGS. 10-24 schematically depict a variety of objects that could be provided with a biocidal plating layer 20 to enhance the performance of the objects.

Figure 10:
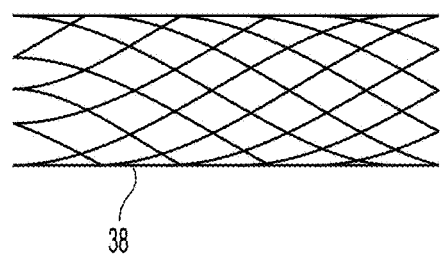
FIG. 10 is a schematic depiction of a stent.
Figure 11:
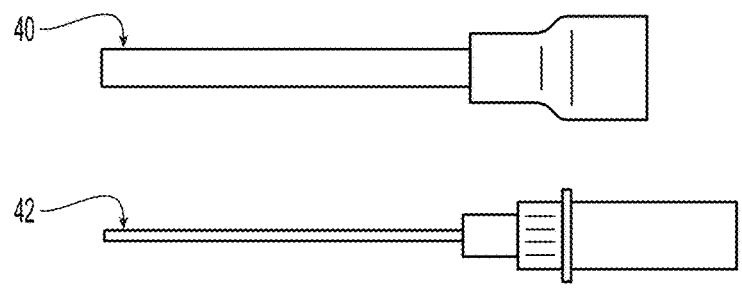
FIG. 11 is a schematic depiction of a catheter and insertion needle.
Figure 12:
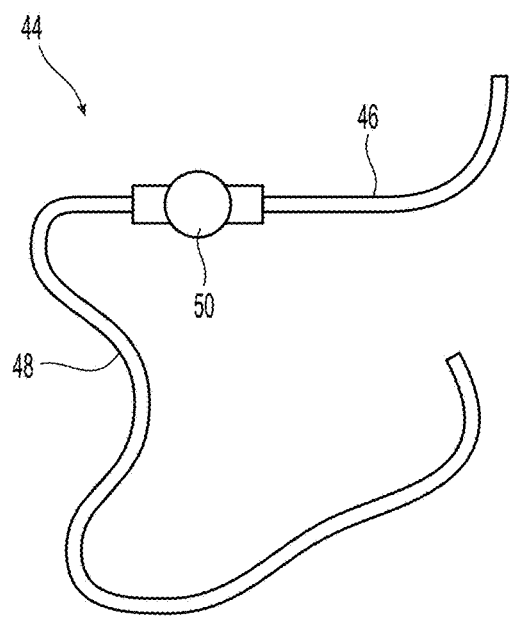
FIG. 12 is a schematic depiction of a shunt.

FIGS. 10-12 all illustrate examples of medical applications wherein a plating layer 20 is applied to an object that is adapted to be implanted in a living organism such as a human being. FIG. 10 illustrates a stent 38 which having an outer plating layer 20. FIG. 11 illustrates a catheter 40 and a catheter needle 42. The metal components of the catheter 40 and catheter needle can beneficially have a plating layer 20 applied thereto. FIG. 12 illustrates a shunt 44 having a proximal catheter 46, a distal catheter 48 and a valve assembly 50. The metal components of such implantable devices may beneficially have a plating layer 20 applied thereto. Moreover, in some circumstances, it may be beneficial to use a metallic component having a plating layer 20 instead of a component more commonly formed of plastic in such devices. For example, currently many catheters employ plastic tubing. The biocidal properties of plating 20, however, may justify the substitution of a metallic tube with plating 20 for a plastic tube in some catheters.

With regard to shunt 44, it is noted that ventriculoperitoneal shunts are commonly used devices in pediatric patients for hydrocephalus or interventricular hemorrhages. The shunts 44 remain in place for prolonged periods, sometimes for life, and must be tapped periodically for a variety of reasons. A certain percentage of these patients develop an infection at the site where the shunts 44 interface with the cerebrospinal fluid. If the valve assembly 50 at the interface is plated with a layer of biocidal plating 20 this has the potential to reduce the incidence of infection. The test data presented above shows that the plating 20 has excellent bactericidal results with at least some of the organisms that may infect pediatric shunts.

Figure 14:
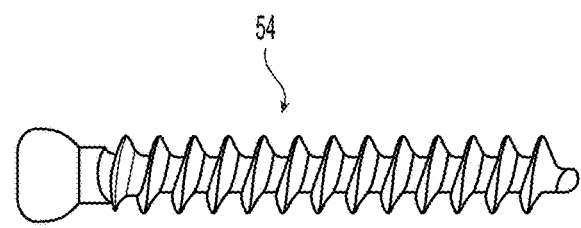
FIG. 14 is a schematic depiction of an orthopedic screw.
Figure 15:
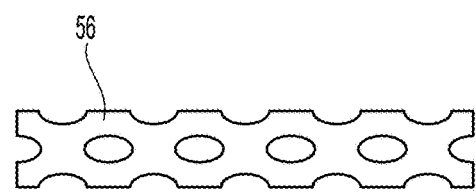
FIG. 15 is a schematic depiction of an orthopedic reconstruction plate.
Figure 13:
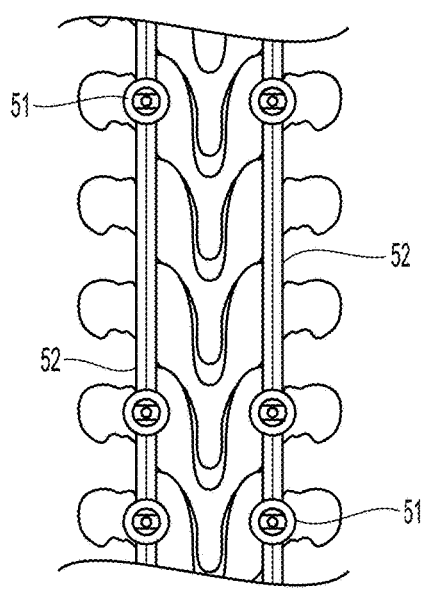
FIG. 13 is a schematic depiction of an orthopedic rod.
Figure 16:
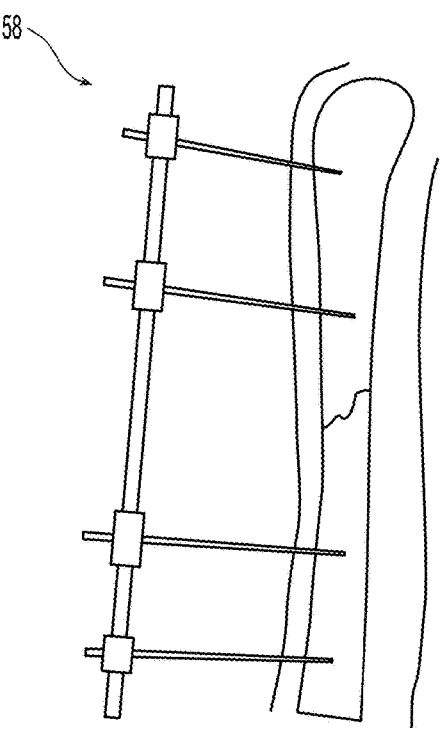
FIG. 16 is a schematic depiction of an orthopedic external fixator.

Orthopedic hardware including implants, external hardware and instrumentation may all benefit from having an external plating layer 20 with biocidal properties. FIGS. 13-16 schematically illustrate examples of such orthopedic hardware having an external plating layer 20. FIG. 13 depicts spinal rods 52 and pedicle screws 51, FIG. 14 depicts a bone screw 54, FIG. 15 depicts a reconstruction plate 56 and FIG. 16 depicts an external fixator 58. Various other orthopedic hardware and instrumentation such as intramedullary rods could also have metal plating 20 applied thereto.

With regard to the use of spinal rods 52 and pedicle screws 51, it is noted that for patients with severe scoliosis, the standard treatment is to install one or more metal rods for several months to years until the curvature is corrected. Sometimes the patient develops an infection around one of the rods. This type of infection can be very difficult to clear with a foreign body such as a rod in place and if it cannot be cleared, the only viable option may be to remove the rod. This may result in an incomplete fusion or instability of the spine and often creates further complication for the scoliosis treatment plan. If the rods were coated with plating 20, this could potentially reduce the incidence of such infections. As mentioned above, the test data presented above shows that the plating 20 shows efficacy against at least two common organisms implicated in such infections.

Figure 17:
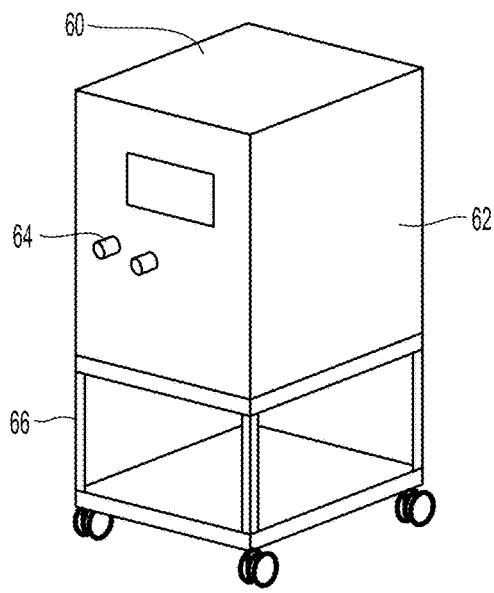
FIG. 17 is a schematic depiction of medical equipment.

As mentioned above, the use of biocidal plating 20 on metal objects that are likely to be handled in a medical facility would be beneficial in reducing infections. Plating 20 can also be used on metal objects in such facilities that are not typically handled to reduce the amount of surfaces in the facility which are conducive to supporting unwanted microorganisms. Examples of such objects are schematically presented in FIGS. 17-20. FIG. 17 depicts a piece of medical equipment 60 that may take the form of a dialysis machine wherein many of the metal components of equipment 60 may have plating 20 applied thereto. For example, housing 62, manual controls 60, such as knobs and switches may all be metal components having an exterior surface formed by metal plating 20. Similarly, support cart 66 may have some or all of its metal parts plated with metal plating 20.

Figure 18:
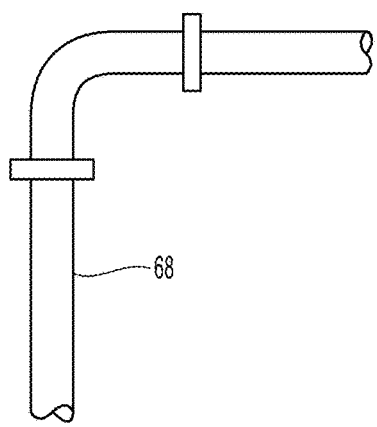
FIG. 18 is a schematic depiction of plumbing.
Figure 19:
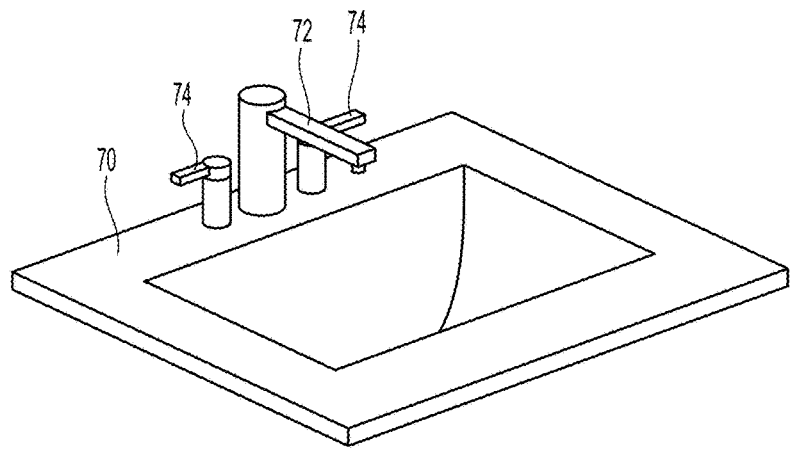
FIG. 19 is a schematic depiction of a faucet and sink.
Figure 20:
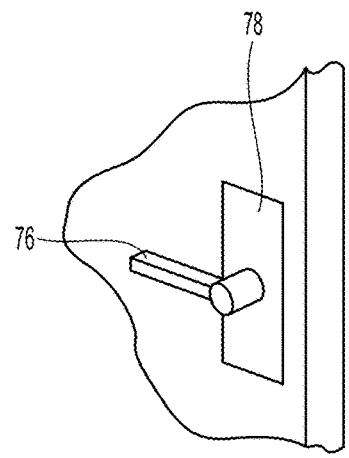
FIG. 20 is a schematic depiction of a door handle.

The various components of the plumbing system in a medical or food preparation facility may also have metal plating 20 applied thereto to reduce the risk of infection. This may include plumbing infrastructure components 68 that are not subject to handling by people on a regular basis. Examples of such plumbing infrastructure is depicted in FIG. 18. It may also include plumbing components that do regularly come into contact with the hands of people within the facility such as those components depicted in FIG. 19. Depicted in FIG. 19 is a sink 70, faucet 72 and handles 74.

Faucet 72 and handles 74 are quite commonly manufactured out of a metal material and would benefit from having a layer of metal plating 20. Sinks 70 may also be formed out of metal material and be provided with a layer of metal plating 20 to inhibit the transfer of microorganisms. Various other forms of metal hardware are found in such facilities and can be beneficially provided with metal plating 20 with those objects being handled the most frequently being those for which plating 20 is most beneficial. For example, door handles 76 (FIG. 20) are one piece of hardware that is subjected to a large amount of handling by persons within a facility and would benefit from the application of metal plating 20. The application of a biocidal metal plating 20 to exposed hardware 78 such as the door handle faceplate depicted in FIG. 20 would also help reduce the transfer and growth of microorganisms even though such hardware may not be subject to extensive handling. As mentioned above, it may be advantageous to utilize a hydrophilic surface treatment on plating layer 20 of such hardware to promote the rapid drying of the plated surface.

Another medical application for plating 20 is illustrated in FIG. 21. FIG. 21 illustrates a baclofen pump 80 having a metal housing 82 with an outer layer formed by biocidal plating 20. Baclofen pumps are used to administer baclofen in a controlled dose to help patients suffering from spasticity from certain diagnoses like cerebral palsy. The pumps are implanted under the skin in a pocket in the abdominal area. Sometimes the pocket site around the pump becomes infected, necessitating surgical removal and prolonged antibiotic therapy. If the pump casing is coated with a plating layer 20, this could potentially reduce the incidence of infection in such patients.

FIG. 22 illustrates another medical application for metal plating 20. This exemplary embodiment takes the form of a dialysis port 84 having a metal port member 86 with a coating of plating 20. Adult dialysis patients are often fitted with a graft with an access port that is used to administer their hemodialysis treatment. Infection of these ports is quite common. Currently, the ports are typically made out of plastic materials. By making the ports 86 out of a metal material and plating the ports with metal plating 20, it may be possible to obtain a reduction in infections at the port site.

The use of plating 20 in a food processing facility is represented in FIGS. 23 and 24. In FIG. 23, a storage vessel 88 is depicted. Both the inner and outer surfaces of vessel 88 may advantageously include a layer of plating 20 to potentially reduce the risk of contaminating the food being stored in the vessel and being processed in the facility.

FIG. 24 schematically depicts a food processing line 90 having a dispensing station 92, a conveyor system 94 and a weighing and packaging station 96. The various metal components of these stations and systems may be advantageously coated with plating 20. It is thought that such an application of plating 20 will reduce the potential for contamination of the food being processed.

In addition to the equipment directly associated with the storage, handling and processing of food, food processing facility may also be able to reduce the threat of contamination by applying a biocidal plating on metal fixtures throughout the facility in a manner similar to that discussed above with regard to medical care facilities. For example, plumbing system components could be plated with metal plating 20 as exemplified by FIGS. 18 and 19. It may also be possible to reduce the threat of contamination by the application of a biocidal plating 20 to metal hardware subject to handling or simply exposed to the surrounding environment in the food processing facility as exemplified by FIG. 20.

For such objects in food processing facilities, it may be advantageous to use a hydrophilic surface treatment on plating layer 20 where the object is regularly cleaned and dried, e.g., daily, such as a table top on which food materials are handled or the housing of a piece of equipment. For other objects, such as the interior surface of a storage vessel that holds a liquid or moist material, where the plating layer 20 is expected to remain exposed to a wet or moist environment on a substantially constant basis and are only intermittently cleaned, e.g., less than daily cleaning, the use of a hydrophobic surface treatment on plating layer 20 may be advantageous.

While this invention has been described as having an exemplary design, the present invention may be further modified within the spirit and scope of this disclosure. This application is therefore intended to cover any variations, uses, or adaptations of the invention using its general principles.

What is claimed is:

1. A device for inhibiting the transmission of microorganisms, said device comprising:
   an orthopedic implant adapted to be implanted in a living organism; and
   a metal plating disposed on the orthopedic implant and forming at least a portion of the exterior surface of the orthopedic implant, the metal plating comprising (by weight):
   copper within a range of about 45% to about 50%;
   tin within a range of about 40% to about 45%; and
   zinc within a range of about 5% to about 10%.

2. The device of claim 1 further comprising a hydrophobic surface treatment layer disposed on the metal plating.

3. The device of claim 1 wherein the orthopedic implant comprises an orthopedic rod.

4. The device of claim 1 further comprising a hydrophilic surface treatment layer disposed on the metal plating.

5. The device of claim 1 wherein the metal plating comprises approximately 45% copper, approximately 45% tin and approximately 10% zinc.

6. The device of claim 5 wherein the device includes a hydrophobic surface treatment layer disposed on the metal plating.

7. The device of claim 1 wherein the metal plating has a mechanically unprocessed exterior surface whereby the mechanically unprocessed surface defines small scale irregularities.

8. The device of claim 6 wherein the metal plating has a mechanically unprocessed exterior surface whereby the mechanically unprocessed surface defines small scale irregularities.

* * * * *